(12) United States Patent
Anderson et al.

(10) Patent No.: US 7,943,185 B1
(45) Date of Patent: May 17, 2011

(54) METHOD AND COMPOSITION FOR PRODUCING A STABLE AND DEODORIZED FORM OF POMEGRANATE SEED OIL

(75) Inventors: Steve Anderson, Fresno, CA (US); Mark Dreher, Woodland Hills, CA (US); Rick Green, Saskatoon (CA)

(73) Assignee: Pom Wonderful, LLC, Los Angeles, CA (US)

( * ) Notice: Subject to any disclaimer, the term of this patent is extended or adjusted under 35 U.S.C. 154(b) by 0 days.

(21) Appl. No.: 11/687,480

(22) Filed: Mar. 16, 2007

(51) Int. Cl.
*A61K 36/00* (2006.01)
(52) U.S. Cl. .......................................... 424/776; 424/725
(58) Field of Classification Search ........................ None
See application file for complete search history.

(56) References Cited

U.S. PATENT DOCUMENTS

| | | | | |
|---|---|---|---|---|
| 3,943,155 | A | * | 3/1976 | Young ........................... 554/190 |
| 4,728,522 | A | * | 3/1988 | Wear et al. .................... 426/242 |
| 5,484,594 | A | | 1/1996 | Frangi et al. |
| 5,891,440 | A | | 4/1999 | Lansky et al. |
| 5,912,363 | A | | 6/1999 | Nafisi-Movaghar et al. |
| 6,060,063 | A | | 5/2000 | Lansky et al. |
| 6,544,581 | B1 | | 4/2003 | Shrikhande et al. |
| 7,417,159 | B2 | | 8/2008 | Galvez et al. |
| 2005/0165105 | A1 | | 7/2005 | Bassaganya-Riera |
| 2007/0116823 | A1 | | 5/2007 | Prakash et al. |
| 2007/0116829 | A1 | | 5/2007 | Prakash et al. |
| 2007/0116838 | A1 | | 5/2007 | Prakash et al. |
| 2007/0116839 | A1 | | 5/2007 | Prakash et al. |
| 2007/0116841 | A1 | | 5/2007 | Prakash et al. |
| 2007/0292582 | A1 | | 12/2007 | Prakash et al. |
| 2008/0107787 | A1 | | 5/2008 | Prakash et al. |

FOREIGN PATENT DOCUMENTS

JP 2002-121581 * 4/2002

OTHER PUBLICATIONS http://www.sciencegeek.net/APchemistry/organic/ochem.shtml—accessed Nov. 13.*

Arao, Keisuke, et al., Dietary effect of pomegranate seek oil rich in 9cis, I I trans, 13cis conjugated linolenic acid on lipid metabolism in obese, hyperlipidemic OLEFT Rats, (2004), 3:24, Nov. 9, 2004, Lipids in Health and Disease.

Aslam, Muhammad Nadeem, et al., Pomegranate as a cosmeceutical source: Pomegranate fractions promote proliferation and procollagen synthesis and inhibit matrix metalloproteinase-1 production in human skin cells, (2006) 311-318, Journal of EthnoPharmacology103.

Van Elswijk, Danny A. et al, Rapid dereplication of estrogenic compounds in pomegranate (*Punica granatum*) using on-line biochemical detection coupled to mass spectrometry, (2004) 233-241, Phytochemistry 65.

Hora, Justin J., et al., Chemopreventive Effects of Pomegranate Seed Oil on Skin Tumor Development in CD1 Mice, 2003, 157-161, Journal of Medicinal Food, J Med Food 6 (3).

Kim, Nam Duek, et al., Chemopreventive and adjuvant therapeutic potential of pomegranate (*Punica granatum*) for human breast cancer, (2002) 71:203-217, Breast Cancer Research and Treatment.

Kohno, Hiroyuki, et al., Pomegranate seed oil rich in conjugated linolenic acid suppresses chemically induced colon carcinogenesis in rats, 2004, 481-486, Cancer Sci, vol. 95.

Lansky, Ephraim Philip, et al., Pomegranate (*Punica granatum*) pure chemicals show possible synergistic inhibition of human PC-3 prostate cancer cell invasion across MatrigeITM, 2005, 121-122, Investigational New Drugs, vol. 23.

Lansky, Ephraim Philip, et al., Possible synergistic prostate cancer suppression by anatomically discrete pomegranate fractions, 2005, 121-122, Investigational New Drugs, vol. 23.

McFarlin, Brian, et al., The Effect of Pomegranate Conjugated Linolenic Acide Supplementation During an Energy-Restricted Diet on Fat Loss and Chronic Inflammation in Previously Obese Mice, Sep. 13, 2006.

Schubert, Shay Y., et al., Antioxidant and eicosanoid enzyme inhibition properties of pomegranate seed oil and fermented juice flavoids, (1999) 11-17, Journal of Ethnopharmacology, 66.

Toi, Masakazu, et al., Preliminary studies on the anti-angiogenic potential potential of pomegranate fractions in vitro and in vivo, (2003) 121-128, Angiogenesis 6.

Yamasaki, Masao, et al., Dietary effect of pomegranate seed oil on immune function and lipid metabolism in mice, (2005), Nutrition.

Yamasaki, Masao, et al., Dietary effect of pomegranate seed oil on immune function and lipid metabolism in mice, (2006) 54-59, Nutrition 22.

Yang, Lin, et al., α-Linolenic acid but not conjugated linolenic acid is hypocholesterolaemic in hamsters (2005) 433-438, British Journal of Nutrition 93.

Mehta, R. and Lansky, E.P., Breast cancer chemopreventive properties of pomegranate (*Punica granatum*) fruit extracts in a mouse mammary organ culture, 2004, 13:345-348, European Journal of Cancer Prevention.

Das, et al. Studies on the hypoglycaemic activity of *Punica granatum* seed in streptozotocin induced diabetic rats, Phytother Res. 15(7):628-9.(Nov. 2001).

(Continued)

*Primary Examiner* — Susan C Hoffman
(74) *Attorney, Agent, or Firm* — Cotman IP Law Group, PLC

(57) ABSTRACT

The present invention provides a method, composition and product by process of pomegranate seed oil. The present invention provides a novel method for the preparation of pomegranate seeds and the subsequent extraction, stabilization and deodorization of pomegranate seed oil. The process maintains key beneficial components of pomegranate seed oil. Effective processing parameters for separating, drying, cleaning, flaking, obtaining the oil from seeds, stabilizing through refining and bleaching and deodorizing the oil are described.

40 Claims, 8 Drawing Sheets

OTHER PUBLICATIONS

Tahraoui, et al. Ethnopharmacological survey of plants used in the traditional treatment of hypertension and diabetes in south-eastern Morocco (Errachidia province), Journal of Ethnopharmacology 110: 105-117 (2007) Available online Sep. 23, 2006.

* cited by examiner

METHOD AND COMPOSITION FOR PRODUCING A STABLE AND DEODORIZED FORM OF POMEGRANATE SEED OIL

BACKGROUND OF THE INVENTION

1. Field of the Invention

One or more embodiments of the invention relate to novel oil fractions extracted from *Punica granatum* (pomegranate) fruit, to the methods and processes for preparation thereof, to compositions containing them and the product created by the method. The invention relates generally to a process for isolating stabilized and deodorized pomegranate seed oil.

2. Description of the Related Art

There are existing processes for isolating oil from fruit seeds. However, pomegranate seed oil is unique. Cold press techniques for isolating pomegranate seed oil yield an unstable and vulnerable product. The product is readily susceptible to decay and goes rancid without hesitation. When applied to pomegranate seeds the standard deodorization and extraction processes for seed oil yields an unstable and readily polymerized product. The pomegranate seed product extracted using standard methods not only has an unpleasant odor but also can form into a gel-like substance making it difficult to use for a variety of products. Pomegranate seed oil has been described as having an "odd flavor" and a "putrid" or "unpleasant" smell. It is thought the high levels of the beneficial constituents in the pomegranate seed oil make it more reactive than other seed oils. Sometimes polymerized oil can be treated with hexane to turn it back into the desirable liquid state. However, this standard technique has proved ineffective with pomegranate seed oil.

Furthermore, since pomegranate seed oil is unstable and goes rancid fairly quickly it minimizes and limits the commercial practicability for the oil. The unstable and negative odor properties of the pomegranate oil results in a product that has little practical use in commercial products such as cosmetics, skin creams, eye creams, dietary supplements and other medicinal applications. Current processes do not yield a useful pomegranate oil product. The present invention defines a process wherein the negative properties of pomegranate seed oil extraction are ameliorated or sufficiently reduced while the beneficial constituents of pomegranate seed oil remain intact.

Pomegranate seed oil contains approximately 65% punicic acid, a conjugated linolenic acid (9cis, 11trans, 13cis-CLNA) and has been reported to possess medicinal properties including anti-carcinogenic activity against breast cancer and skin cancer. The high polyunsaturated fatty acid content, however, makes this oil extremely susceptible to oxidative rancidity. As a result, extraction and refining process parameters typically employed for edible and cosmetic oils may degrade the pomegranate seed oil.

The benefits of pomegranate seed oil have been reported to act in the areas of immune function, cancer prevention and therapy, cardiovascular health, skin health, and healthy lipid metabolism.

Pomegranate seed oil has been mentioned as a treatment for various ailments. It has been shown that pomegranate seed oil has benefits on immune function. Serum, liver, epididymal, and perirenal adipose punicic acid levels were high with increases in dietary pomegranate seed oil levels. However, punicic acid was not detected in splenocytes for any dietary group. The results suggest that pomegranate seed oil may enhance B-cell function in vivo.

Pomegranate seed oil has been implicated in the treatment and prevention of various cancers. Anti-carcinogenic and chemopreventive components have been found in pomegranate seed oil. Findings indicated the chemopreventive activity of pomegranate seed oil as well as an isolated HPLC fraction, referred to as peak B. An effect of pomegranate extracts on inhibiting prostate cancer cell proliferation has been described. The study shows the interactions of the extracts from three pomegranate compartments (peels, juice, seeds) in inhibiting prostate cancer cell proliferation, invasion and phospholipase A-2 (associated with invasive potential) expression. This study indicates the possibilities of pomegranate as a synergistic drug for the treatment of cancer.

Further studies show the potential and chemopreventive nature of pomegranate seed oil. Another study discusses the beneficial role of CLA-rich pomegranate seed oil in colon carcinogenesis. Topical application of pomegranate seed oils has been shown to be an effective chemopreventive treatment for skin cancer. Another study discusses the potential of pomegranate seed oil and polyphenols in fermented pomegranate juice to have an inhibitory effect on oxidation and prostaglandin synthesis, as well as inhibit breast cancer cell proliferation and invasion, and promote apoptosis of breast cancer cells. Further studies indicated pomegranate seed oils containing conjugated linolenic acids (CLN) were cytotoxic to human monocytic leukemia cells.

Pomegranate seed oil is also mentioned as a possible treatment for skin repair. Cosmeceutical applications for pomegranate suggest a potential for certain pomegranate fractions for facilitating skin repair, namely aqueous extracts (especially that from pomegranate peel) for promoting the repair of dermis, and pomegranate seed oil promoting regeneration of epidermis.

Pomegranate seed oil has been indicated in the maintenance of healthy lipid metabolism and cholesterol levels. The hypocholesteroleamic activity of LN (linolenic acid) and CLN (conjugated linolenic acid) have been described. CLN is found in pomegranate seed oil and it had no effect on serum cholesterol. CLN and LN significantly decrease hepatic cholesterol but no effect was observed on heart and kidney cholesterol levels. A report indicates that pomegranate seed oil has an effect on lipid metabolism.

Pomegranate seed oil has been shown to have benefits for cardiac problems and even asthma. A potential role for pomegranate extracts as cardioprotective and an anti-inflammatory medicament for internal and/or external applications have been proposed for treatments such as asthma. Fermented pomegranate juice and cold pressed pomegranate fruit extract can reduce prostaglandin and leukotriene formation by the inhibition of cyclooxygenase and lipozygenase activities. Leukotriene participates in allergic responses and particularly the bronchoconstriction involved in asthma. Pomegranate fractions have an anti-angiogenic potential. More cardio info.

The active components of the pomegranate fruit have begun to be isolated and identified. The presence of estrogenic compounds in pomegranate peel extracts was reported. In this study estrogenic compounds luteolin, quercetin, and kaempferol were detected and identified in the pomegranate peel.

One or more embodiments of the invention maintain the positive qualities of the pomegranate seed oil while minimizing and deleting the less desirable qualities such as unpleasant odor and a short shelf-life. Hence embodiments of the invention may be referred to generally as a process of stabilizing and deodorizing pomegranate seed oil.

BRIEF SUMMARY OF THE INVENTION

One or more embodiments of the invention are directed to a method, a composition and a product by process for manufacturing a stabilized form of pomegranate seed oil.

One or more embodiments of the invention are directed to a method for extracting oil from *Punica granatum* seeds to formulate a stable and deodorized pomegranate seed oil. The method generally directed to a process that involves separating, drying, cleaning, flaking, and selecting a method for obtaining the *Punica granatum* seeds.

The process of separating is the initial step and generally makes use of any acceptable method for separating the *Punica granatum* seeds from a mash.

The drying step is accomplished by applying heat to the seeds through the use of a forced air dryer or other mechanism for reducing the water level within the seeds. When using the forced air embodiment drying is initiated for a duration and temperature sufficient to achieve optimal peroxide value and/or optimal free fatty acid content. This is generally accomplished by drying the seeds for a set duration of time at a set temperature range. For instance, the drying can occur for a set duration of 3 to 9 hours and the set temperature range may be between 80-110° C. Drying of the *Punica granatum* seeds may occur by placing *Punica granatum* seeds at a set depth in a forced air dryer for the set time at a set temperature. The set depth of forced air oven may be ½". The set temperature may be between 95-100° C. And the set time may range between 3 to 5 hours. Generally drying is performed until the *Punica granatum* seeds contain 5-8% moisture content or less than 8% moisture content.

The cleaning step generally involves cleaning the *Punica granatum* seeds via a shaker deck and air aspiration. When air aspiration is used it is typically done under a vacuum of 1.2" of water. Other methods of cleaning the seeds are however still within the scope and spirit of the invention and any such means that accomplishes this goal is acceptable.

Flaking of the *Punica granatum* seeds comprises tempering the seeds from 16% moisture content by applying steam and adjusting the temperature to 70° C. Flaking the *Punica granatum* seeds may produce flakes of approximately 0.5 mm in thickness and is accomplished in at least one embodiment of the invention by pre-heating seeds to 50±3° C. in a cooker section of a cooker pre-press then flaking using a roller gap width setting of 0.2 mm.

Selection of a method for obtaining *Punica granatum* seed oil may comprise extracting of seed oil from the *Punica granatum* seeds using solvent extraction using 1-methyl pentane mixed with 50 to 1,000 ppm mixed tocopherols on a counter-current extractor. Other natural antioxidants (e.g. Rosemary) or synthetic antioxidants (e.g. BHA/BHT) may also be used. The selecting of method for obtaining *Punica granatum* seed oil may comprise extracting of seed oil by applying external pressure to the *Punica granatum* seeds.

Stabilizing of the *Punica granatum* seed oil generally comprises a refining and bleaching step. Refining may be achieved by caustic refining and/or refining by water washing. Stabilizing of the *Punica granatum* seed oil may comprise refining by heating to 65° C. and adding 0.1% phosphoric acid, mixing and adding sodium hydroxide at 1 to 4% of starting oil weight. Stabilizing of the *Punica granatum* seed oil may comprise refining by clarifying mixture by heating to 40 to 90° C. and centrifuging adding 15% water (w/w) and mixing at 75° C. The stabilizing of the *Punica granatum* seed oil may comprise refining by recovering oil from water wash by centrifugation and involve a bleaching step that makes use of bleaching clay or any other acceptable bleaching means. Bleaching may occur by applying heat, adding citric acid and mixing. Stabilizing of the *Punica granatum* seed oil may make use of bleaching by pre-heating oil to 65° C. The stabilization step may also involve bleaching by adding 0.2% citric acid and mixing for 15 minutes. Achieving stabilization may generally involve bleaching by using a cellulose-acetate filter aid and adding clay or activated carbon and mixing for 15 minutes. The bleaching step may involve adding clay at 0.5% to 5% or activated carbon at 75-115° C. for 10 to 60 minutes in a reactor under full vacuum; and bleaching by cooling oil to 65° C. and filtering through filter elements.

Deodorizing the *Punica granatum* seed oil is also part of the process and may comprise putting the *Punica granatum* seed oil under vacuum pressure and heating to a set temperature for a set duration of time. Deodorizing of the *Punica granatum* seed oil involves placing the bleached seed oil under of vacuum pressure of 18-28 mm Hg, heating the seed oil to a temperature range between 180-210° C. for a range of approximately 30 to 120 minutes and steaming and/or nitrogen sparging. A cooling step is then performed that involves cooling the seed oil to 40-90° C. and filtering through a coarse filter. An antioxidant mixture of TBHQ, tocopherols, and ascorbyl palmitate may also be added to the seed oil as part of the process described herein.

DETAILED DESCRIPTION OF THE INVENTION

The following descriptions of one or more embodiments of the invention are exemplary, rather than limiting, and many variations and modifications are within the scope and spirit of the invention. Although numerous specific details are set forth in order to provide a thorough understanding of the present invention, it will be apparent to one of ordinary skill in the art, that embodiments of the invention may be practiced without these specific details. In other instances, well-known features have not been described in detail in order to avoid unnecessarily obscuring the invention which is directed to processes for the preparation of pomegranate seeds and the extraction, stabilization, and deodorization of pomegranate seed oil. The processes provide a technique wherein the beneficial components of pomegranate seed oil remain intact subsequent to processing.

One or more embodiments of the invention are directed to a unique method, composition and a product by process for pomegranate seed oil.

Figure 1:
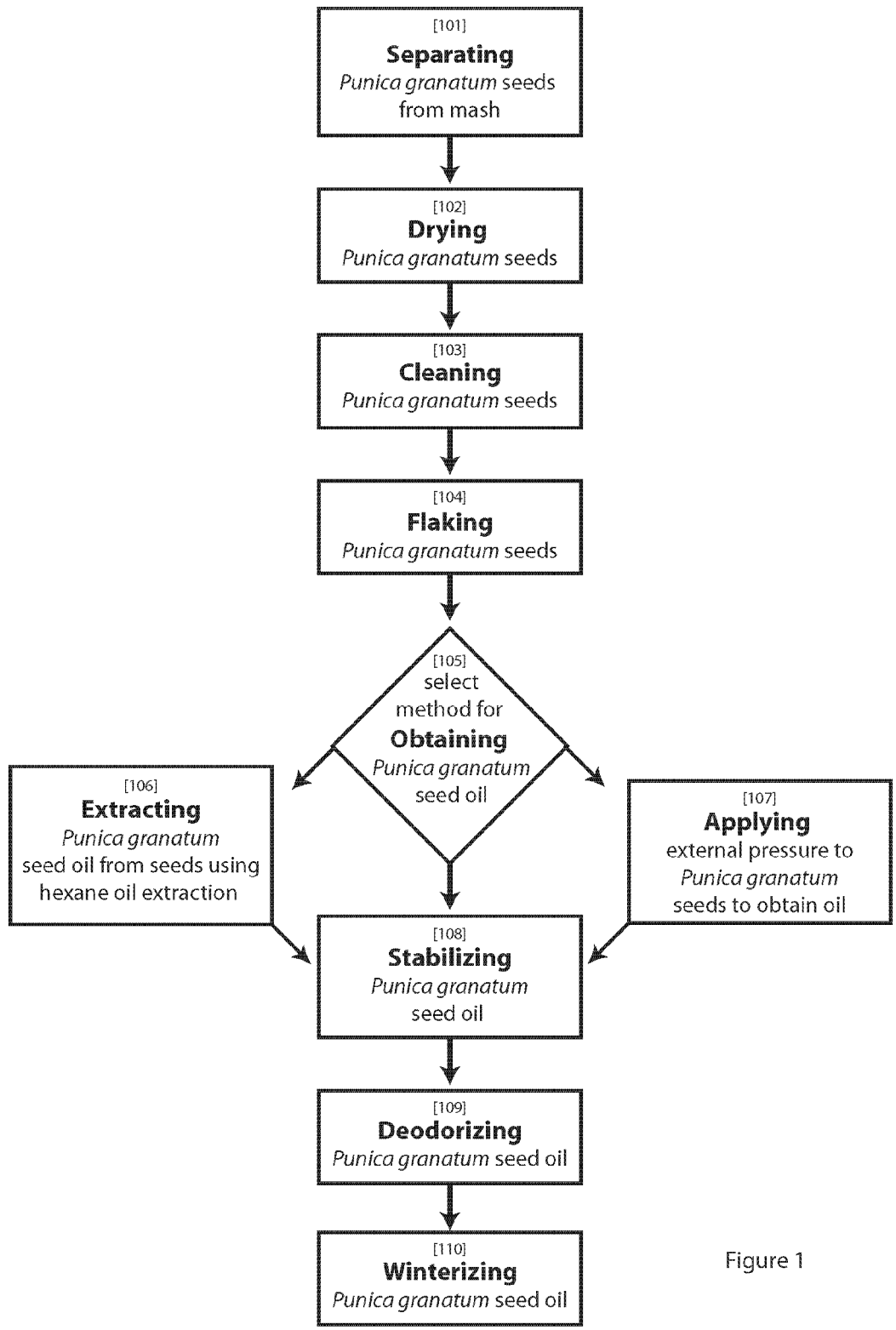
FIG. 1 illustrates the method of isolating and obtaining, stabilizing and deodorizing *Punica granatum* seed oil.

Generally, as depicted in an overview in FIG. 1, the processes of the invention are characterized by the following steps:

Separating [101], Drying [102], Cleaning [103], Flaking [104], Obtaining [105] by extracting [106] or applying pressure [107], Stabilizing [108], and Deodorizing [109].

These steps are depicted in further detail throughout the application.

SEPARATING. Separating is shown in the first block of FIG. 1. One or more embodiments of the invention involve separating pomegranate seeds from a mash of pomegranate fruit [101].

Figure 2:
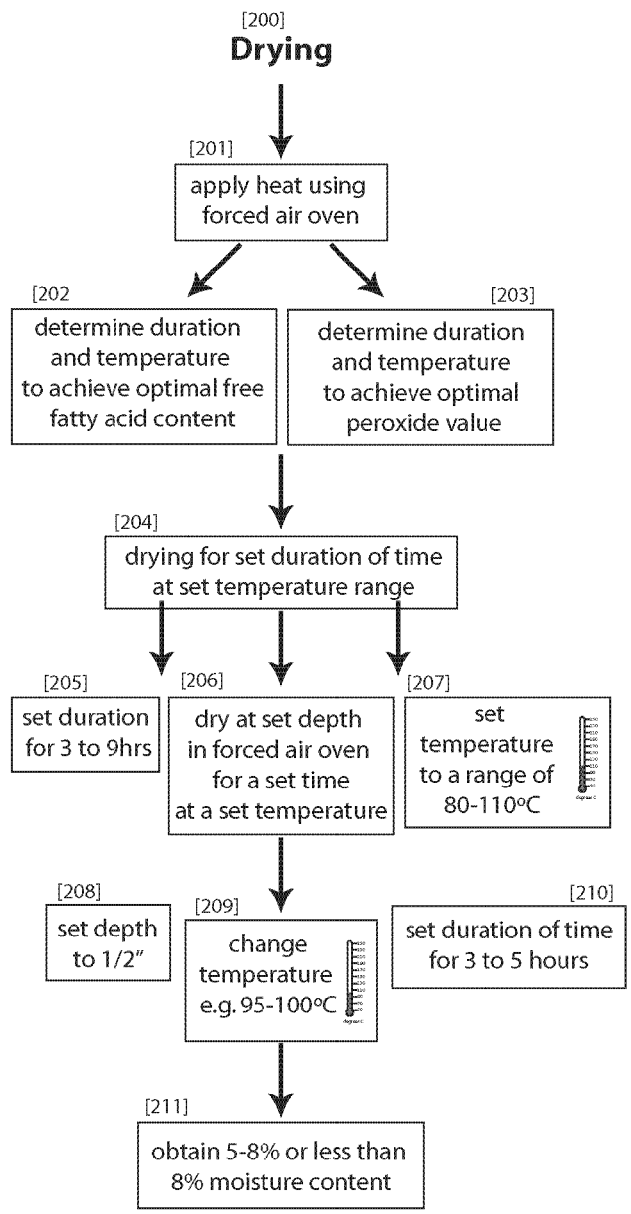
FIG. 2 illustrates the method of drying the seeds of *Punica granatum*.

DRYING. The drying step is shown in block 2 of FIG. 1 and further depicted in detail in FIG. 2. One or more embodiments of the invention involve a drying step for purposes of removing moisture from the pomegranate fruit seeds from which the seed oil is to be extracted. Moisture removal may be carried out using any acceptable process but is achieved in at least one embodiment of the invention by placing pomegranate seeds in a forced air dryer [201]. Moisture removal may occur for a duration and temperature to achieve optimal free fatty acid content [202] and/or optimal peroxide value [203]. Moisture removal may occur for a set duration of time at a set temperature range [204] and occur at a set depth in a forced air dryer for a set time at a set temperature [206]. The set temperature range of 80-110° C. [207] is generally acceptable for achieving the proper level of drying when drying is done for a duration of 3 to 9 hours [205]. More specifically but not by way of limitation moisture removal may be carried out by placing the pomegranate seeds in a forced air tunnel dryer at a depth of ½" at 100±5° C. for a time of 3 to 5 hours to yield seeds with 5-8% or less than 8% moisture content [208, 209, 210, 211].

Figure 3:
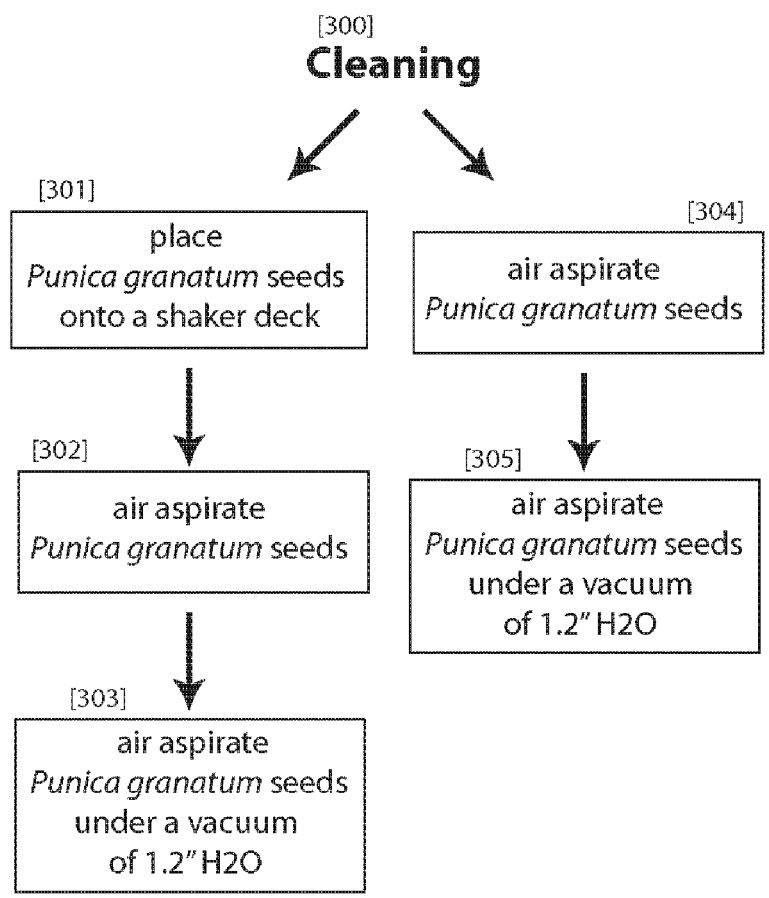
FIG. 3 illustrates the method of cleaning the seeds of *Punica granatum*.

CLEANING. The cleaning step is shown in block 3 of FIG. 1 and further depicted in detail in FIG. 3. Dried pomegranate seeds can contain dried pulp and skin fragments. It is generally beneficial to remove these unwanted materials from the pomegranate seeds via a cleaning step. Removal of unwanted dried material is carried out in at least one embodiment of the invention by placing *Punica granatum* seeds onto a shaker deck [301]. An air aspirator [302, 304] is also helpful when seeking to remove these unwanted materials. When using an air aspirator application is typically performed under a vacuum of 1.2" of water [303] to yield cleaned dried seed free of pulp and skin fragments. The removal of unwanted material after solvent oil extraction can yield oil that is lighter in color requiring a less rigorous bleaching regimen. To summarize the removal of unwanted dried material from the seeds may be carried out by placing seeds onto a shaker deck, air aspiration, and air aspiration under a vacuum or 1.2" of water [301, 302, 303].

Figure 4:
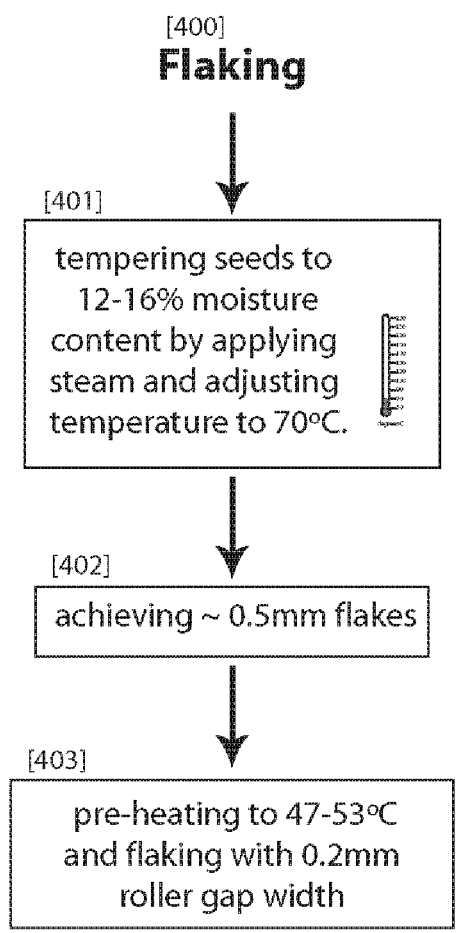
FIG. 4 illustrates the method of flaking the seeds of *Punica granatum*.

FLAKING. The flaking step is shown in block 4 of FIG. 1 and further depicted in detail in FIG. 4. The conversion of pomegranate seed into particles may be referred to as flaking [104, 400]. The conversion into particles may occur prior to solvent extraction with pomegranate seeds tempered to 12-16% moisture content [401] by using steam and adjusting temperature to 70° C. The flaking may produce ~0.5 mm flakes [402]. Flaking is carried out in accordance with one or more embodiments of the invention by heating the pomegranate seed to a temperature between 47-53° C. [403]. Pre-heating the pomegranate seed to 50±3° C. in the cooker section of a cooker pre-press is generally advisable followed by flaking immediately thereafter using a roller gap width setting of 0.2 mm or other setting acceptable to accomplish the goal of flaking [403]. In the case that seed flaking results in excessive production of fines the moisture content may be adjusted by applying steam and changing the temperature to 70° C. For instance, ideal flaking conditions may produce large consistent flakes, 0.50±0.5 mm in thickness and 13.0±0.5% moisture content. From a 325 kg batch of tempered seed a yield of 310.9 kg of flaked pomegranate seed may be produced.

Figure 5:
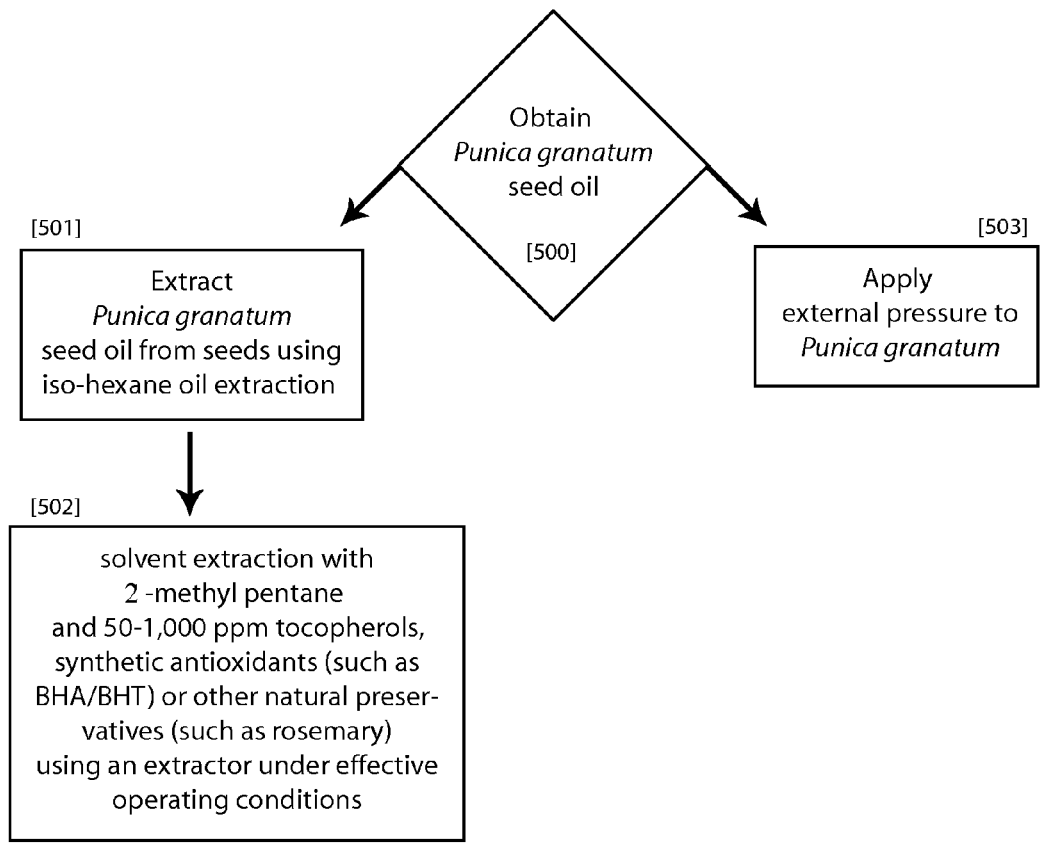
FIG. 5 illustrates the method of obtaining the seed oil from the seeds of *Punica granatum*.

OBTAINING. The obtaining step is shown in block 5 of FIG. 1 and in further detail in FIG. 5. Drawing forth of seed oil from flaked pomegranate seed is generally accomplished by applying external pressure [107, 503] and/or through the use of solvent extraction using iso-hexane [106, 501]. For example, 2 methylpentane (isohexane) [502] generally serves as a reliable solvent for extracting the seed oil. The drawing forth of seed oil from flaked pomegranate seed may be carried out by solvent extraction using 2-methylpentane (isohexane) with 50-1,000 ppm tocopherols or other natural antioxidants such as Rosemary or synthetic antioxidants such as BHA/BHT [502]. The solvent extraction may be carried out using an extractor (such as a Soxhlet) wherein pomegranate seed flakes can be loaded in to the screen sample holder and extracted for four hours to result in an extraction yield of greater than 95%. The solvent extraction may be carried out in 2-methylpentane on a counter-current extractor (such as Crown) under effective operating conditions. The effective operating conditions for a counter-current extractor may be the following: Flake feed rate 65 Kg/h, Retention time of 60 minutes, Bed level setting at minimum, fresh solvent flow 150±5 Kg/h, Solvent temperature 52±4° C., RFE feed rate 21 pm, RFE steam pressure 13 psi, DT sparge steam off, DT top tray temperature 84±3° C., DT bottom tray temperature 100±2° C. The solvent extraction may contain the addition of mixed tocopherols to 2-methylpentane to minimize oxidation of the oil. Mixing in tocopherols or other antioxidants may be added at a quantity of 50 to 1,000 ppm. The extraction may yield crude oil that has a PV of 0.69, FFA of 1.54%, and Lovibond color parameters (1 inch sample cell) 70.0Y and 2.9R.

Figure 6:
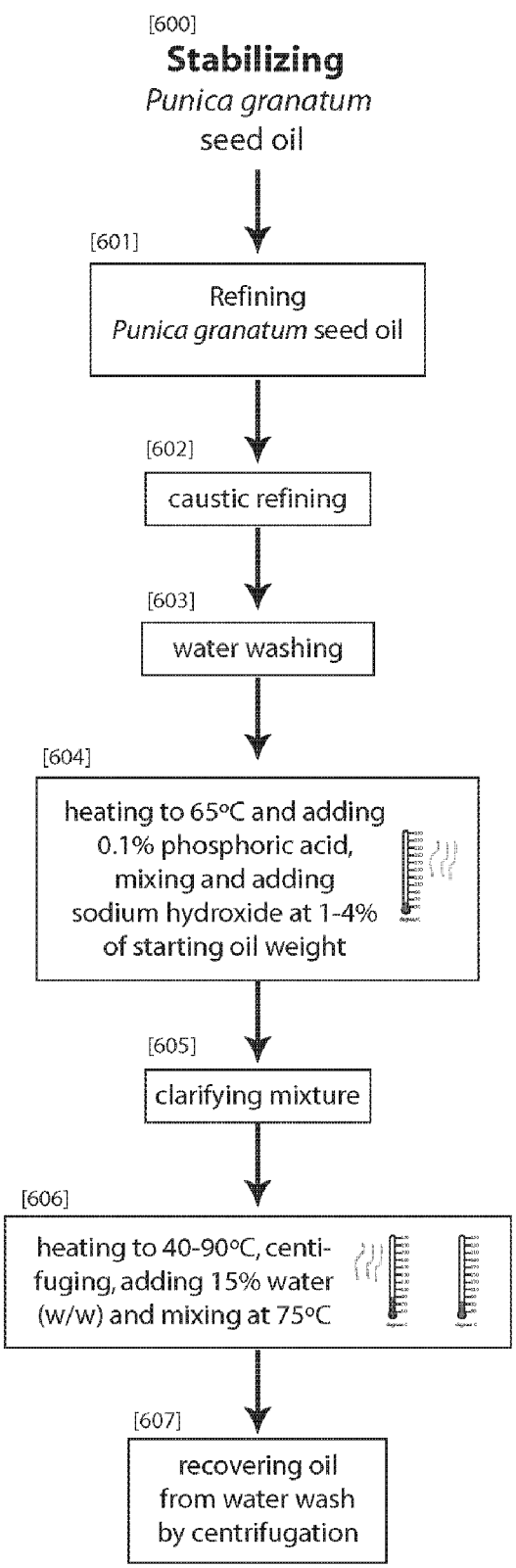
FIG. 6 illustrates the method of stabilizing *Punica granatum* seed oil.

STABILIZING (refining). The stabilizing step is shown in FIG. 1 and in further detail in FIG. 6 and FIG. 7. Stabilizing has two major components refining, shown in FIG. 6, and bleaching, shown in FIG. 7. One or more embodiments of the invention are directed to a unique process for stabilizing isolated *Punica granatum* seed oil [108, 600, 700]. FIG. 6 depicts further detail of the refining step of the stabilizing process [600]. The general objective in refining is to free the extracted pomegranate seed oil from impurities and/or unwanted material [601]. The impurities may be caustic, black sediment, or otherwise undesirable material. The process for freeing the impurities is generally referred to as refining or caustic refining [602]. Stabilizing the *Punica granatum* seed oil may require caustic refining. Crude oil extracted from pomegranate seed flakes may contain undesirable material. The stabilization may involve water washing [603] and require assessment of the need for refining the oil; Free fatty acid (FFA) values may indicate a need for caustic refinement of the oil. FFA values may be near 1.54% indicating a need for further refinement. Such refining is generally carried out by heating the crude pomegranate seed oil to 65° C. and adding 0.1% phosphoric acid. The mixture of crude pomegranate seed oil and phosphoric acid may then be mixed for 15 minutes and sodium hydroxide (18 Be) may be added at 1-4% of the starting oil weight [604]. The mixture may then be clarified [605] by heating to 40 to 50° C. and applying centrifugation [606] to remove undesirable black sediment and other impurities from the oil. After the clarifying 15% (w/w) may be added and mixed for 15 minutes at 75° C. [606]. Oil may be recovered from water wash by centrifugation [607]. This process may yield an FFA value of the caustic refined and water washed oil of less than 0.5%. The refining process may include a winterization step wherein refrigeration is applied to facilitate wax removal.

Figure 7:
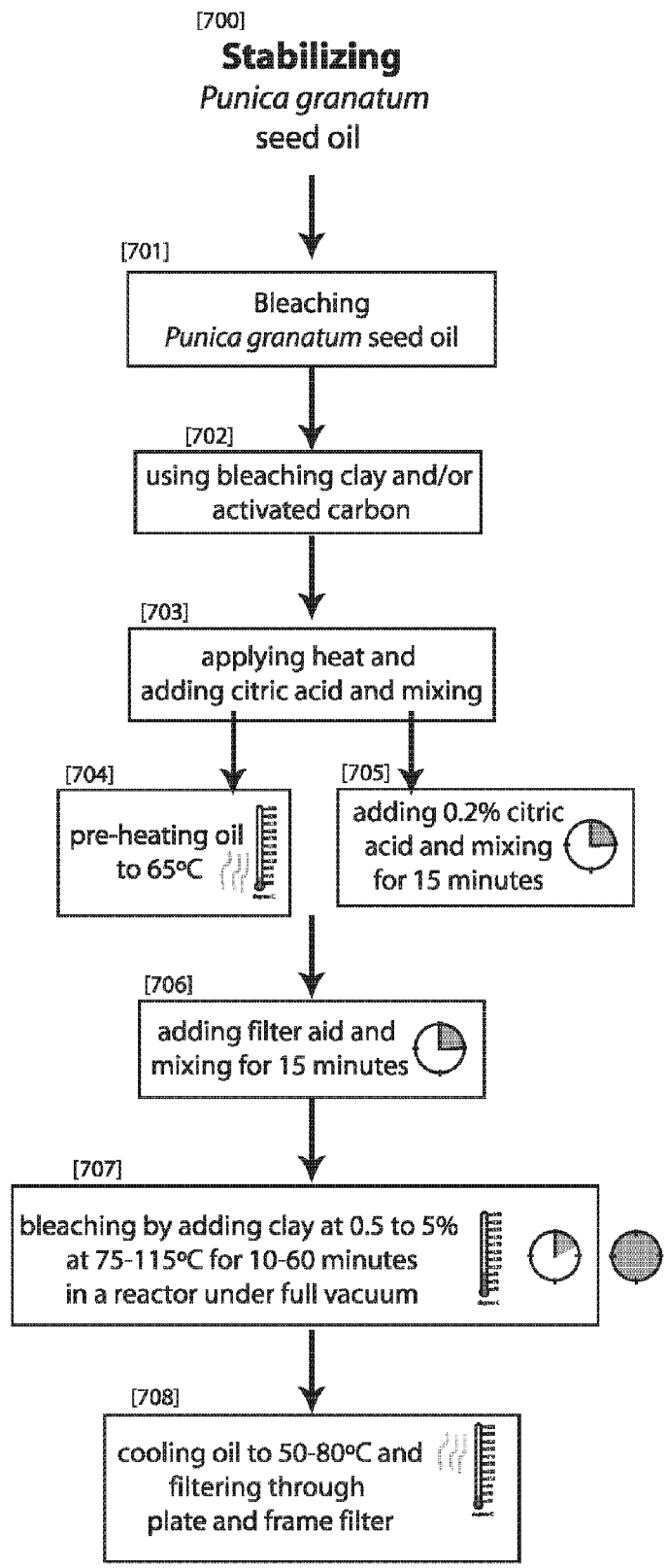
FIG. 7 further illustrates the method of stabilizing *Punica granatum* seed oil.

STABILIZING (Bleaching). As previously stated stabilizing requires a two-fold process of refining and bleaching. FIG. 7 depicts further detail of the bleaching aspect of the stabilizing process [700] which generally lightens or removes color from the pomegranate seed oil [701]. This process of lightening or removal of color is generally referred to as bleaching [701]. The bleaching may be carried out using bleaching clay or activated carbon [702], applying heat and adding citric acid and mixing [703] and pre-heating oil to 65° C. [704]. Quantities of 0.2% citric acid are typically effective when mixing [705]. A filter aid (e.g. cellulose acetate) and mixing [706] is also beneficial. When adding clay 0.5-5% clay at 75-115° C. for 10-60 minutes in a reactor under full vacuum [707] is effective. Cooling the oil to 50 to 80° C. and filtering [708] also produces results. While any means for bleaching is acceptable, bleaching is generally carried out in a reactor (such as Parr) using various grades of bleaching clay and may undergo the following exemplary steps. Oil may be pre-heated to 65° C. and 0.2% citric acid may be added and mixed for 15 minutes. Trisyl S615 filter aid (0.2% w/w) may be added and mixing continued for another 15 minutes. Bleaching clay (%3, w/w) may then be mixed into the oil and the reactor sealed. Bleaching may be performed at 95° C. for 30 minutes under full vacuum. The oil may then be cooled to 65° C. and filtered. The bleaching may be carried out using bleaching clay such as Tonsil Supreme 124FF and undergo the following steps: Oil can be heated to 65° and 0.2% citric acid added and mixed for 15 minutes. Trisyl S615 filter aid (0.2%, w/w) can be added and mixing continued for an additional 15 minutes. Bleaching clay (3%, w/w) may then be mixed into the oil and the reactor sealed. Bleaching may be performed at 95° C. for 30 minutes under full vacuum in a mini-RBD bleaching reactor. The oil may then be cooled to 65° C. and filtered. The above mentioned steps may effectively lighten the color of the oil to achieve Lovibond Y and R values of 2.0 and 0.2, respectively.

Figure 8:
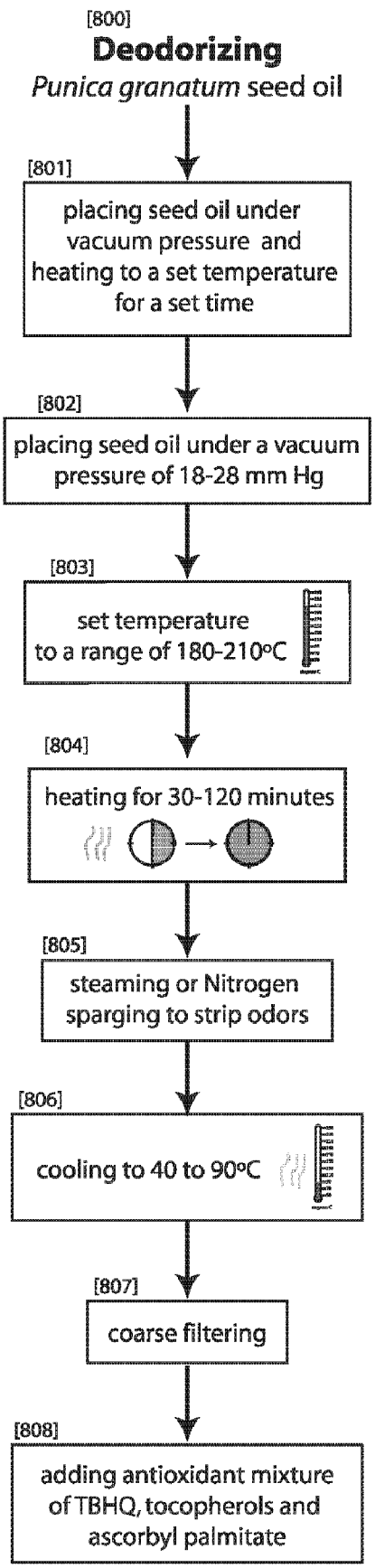
FIG. 8 illustrates the method of deodorizing *Punica granatum* seed oil.

DEODORIZATION. Deodorization is shown in FIG. 1 and in FIG. 8 in further detail [800]. One or more embodiments of the invention make use of a deodorizing step to remove unpleasant qualities of pomegranate seed oil such as its offensive odor when extracted in raw form. The elimination or prevention of offensive odor of pomegranate seed oil is referred to as deodorizing. FIG. 8 depicts the process of deodorizing in detail [800]. Deodorizing is generally carried out by placing seed oil under vacuum pressure (e.g., 18-28 mm Hg [802]) and heating the seed oil to a set temperature (e.g., 180-210° C. [803]) for a set time [801] such as 30-120 minutes and sparging using steam or nitrogen gas [804, 805]. The deodorizing step also involves cooling the seed oil to 40-90° C. and coarse filtering [806, 807]. An antioxidant mixture such as tert-butylhydroxyquinone (TBHQ) at 50-200 ppm, tocopherols at 50-200 ppm and/or acrobyl palmitate at 50-200 ppm [808] is generally helpful. Other quantities of tocopherol, TBHQ and ascobyl palminate are however also within the scope and spirit of the invention. The elimination or prevention of offensive odor of pomegranate seed oil may be carried out by heating the oil using a heating apparatus and vacuum to a target temperature range below 210° C. The deodorization may occur by taking bleached pomegranate seed oil under vacuum pressure (28-30 mm Hg) and heating it to a temperature between 180-210° C. for 30 to 120 minutes. The preferred deodorization residence time range is 30 to 60 minutes.

The present invention provides a novel process that allows for the preparation of pomegranate seeds and the subsequent extraction, stabilization and deodorization of the polyphenol rich pomegranate seed oil.

The present method comprises a number of separate phases, which, taken together, produce the beneficial result. However, it will readily appreciated that the division of the method into separate phases is an artificial construct, primarily to aid in the clarity of presenting the invention, and that various aspects of any particular phase may be performed out of the described order, or combined with aspects ascribed to other phases, while still obtaining the benefits of the invention.

The method for making pomegranate seed oil includes the processing steps of separating, drying, air aspiration, flaking, obtaining seed oil, stabilizing which includes refining and bleaching and deodorization.

DEFINITIONS

As used herein "pomegranate seed oil" refers to or means a substance derived and prepared from the components of the pomegranate seed. The substance may be an extract of the pomegranate seed wherein it is a powder, a liquid, a juice, mixed in a solution, a pill, a solid, from a raw pomegranate fruit, from a fermented pomegranate fruit. The extract may contain enhanced polyphenols beyond that which is naturally within the extracted substances. The extract may contain enhanced conjugated linolenic acids, including but not limited to punicic acid.

As used herein "polyphenols" refers to or means but not is limited to a polyhydroxy phenol; especially an antioxidant phytochemical that tends to prevent or neutralize the damaging effects of free radicals.

As used herein, the terms "reduces," "reduced," or "reducing," when used to refer to a particular odor or taste characteristic, refers to any observable lessening of that characteristic when the method or composition of the present invention is compared to prior art methods or compositions.

As used herein, the terms "odor," "smell," and "scent" refer to olfactory recognition of any particular or group of particular gases. Preferably, the olfactory recognition refers to mammalian, and most preferably human, olfactory recognition. Such recognition was determined by observation by the inventors, and may alternatively be determined by a cross-section of the population or by quantitative or qualitative recognition devices known to those of skill in the art.

Thus, while embodiments and alternatives have been disclosed and discussed, the invention herein is not limited to the particular disclosed embodiments or alternatives but encompasses the full breadth and scope of the invention including equivalents, and the invention is not limited except as set forth in and encompassed by the full breadth and scope of the claims herein:

What is claimed is:
1. A method for extracting seed oil from *Punica granatum* seeds to formulate a stabilized seed oil, said method comprising:
    separating *Punica granatum* seeds;
    drying said *Punica granatum* seeds;
    cleaning said *Punica granatum* seeds;
    flaking said *Punica granatum* seeds, wherein said flaking comprises tempering said seeds to 12 to 16% moisture content;
    extracting *Punica granatum* seed oil from said *Punica granatum* seeds on a counter-current extractor using solvent extraction using isohexane mixed with 50 to 1,000 ppm antioxidants selected from at least one of the group consisting of mixed tocopherols, natural antioxidants, and synthetic antioxidants; and
    stabilizing said *Punica granatum* seed oil.
2. The method of claim 1 further comprising:
    deodorizing said *Punica granatum* seed oil; and
    winterizing said *Punica granatum* seed oil.

3. The method of claim 2 wherein said deodorizing of said *Punica granatum* seed oil comprises placing said *Punica granatum* seed oil under vacuum pressure and heating to a set temperature for a set duration of time.

4. The method of claim 2, wherein said stabilizing of said *Punica granatum* seed oil comprises bleaching, and wherein said deodorizing of said *Punica granatum* seed oil comprises placing said bleached seed oil under a vacuum pressure of 18-28 mm Hg.

5. The method of claim 2 wherein said deodorizing of said *Punica granatum* seed oil comprises heating to a temperature range between 180-210° C.

6. The method of claim 2 wherein said deodorizing of said *Punica granatum* seed oil comprises heating for a duration between the range of 30 to 120 minutes and steaming and/or nitrogen sparging.

7. The method of claim 2 wherein said deodorizing of said *Punica granatum* seed oil comprises cooling deodorized oil to 40-90° C. and filtering through a coarse filter.

8. The method of claim 1 wherein said separating of said *Punica granatum* seeds comprises separating said *Punica granatum* seeds from mash.

9. The method of claim 1 wherein said drying said *Punica granatum* seeds comprises applying heat through use of a forced air dryer.

10. The method of claim 1 wherein said drying said *Punica granatum* seeds is initiated for a duration and temperature sufficient to achieve a free fatty acid content of less than 0.5%.

11. The method of claim 1 wherein said drying said *Punica granatum* seeds comprises drying for a set duration of time at a set temperature range.

12. The method of claim 11 wherein said set duration is greater than 3 hours.

13. The method of claim 11 wherein said temperature range is between 80-110° C.

14. The method of claim 11 wherein said drying said *Punica granatum* seeds comprises placing *Punica granatum* seeds at a set depth in a forced air dryer for a set time at a set temperature.

15. The method of claim 14 wherein said set depth of forced air dryer is ½".

16. The method of claim 14 wherein said set temperature is between 95-100° C.

17. The method of claim 14 wherein said set time ranges between 3 to 5 hours.

18. The method of claim 1 wherein said drying said *Punica granatum* seeds comprises:
drying until said *Punica granatum* seeds contain 5-8% moisture content.

19. The method of claim 1 wherein said cleaning said *Punica granatum* seeds comprises use of shaker deck and air aspiration.

20. The method of claim 1 wherein said cleaning said *Punica granatum* seeds comprises use of air aspiration.

21. The method of claim 1 wherein said cleaning said *Punica granatum* seeds comprises using air aspiration under a vacuum of 1.2" of water.

22. The method of claim 1 wherein said flaking said *Punica granatum* seeds produces flakes of approximately 0.5 mm in thickness.

23. The method of claim 1 wherein said flaking said Punica granatum seeds further comprises:
pre-heating said tempered seeds to 50±3° C. in a cooker section of a cooker pre-press; and
flaking said tempered seeds using a roller gap width setting of 0.2 mm.

24. The method of claim 1 wherein said stabilizing of said *Punica granatum* seed oil comprises refining and bleaching.

25. The method of claim 1 wherein said stabilizing of said *Punica granatum* seed oil comprises refining.

26. The method of claim 1 wherein said stabilizing of said Punica granatum seed oil comprises caustic refining.

27. The method of claim 1 wherein said stabilizing of said *Punica granatum* seed oil comprises refining by water washing.

28. The method of claim 27 wherein said refining comprises recovering oil from said water washing by centrifugation.

29. The method of claim 1 wherein said stabilizing of said *Punica granatum* seed oil comprises refining by heating to 65° C. and adding 0.1% phosphoric acid, mixing and adding sodium hydroxide at 1 to 4% of starting oil weight.

30. The method of claim 1 wherein said stabilizing of said *Punica granatum* seed oil comprises refining by heating to 40 to 50° C. and centrifuging to remove impurities, followed by adding 15% water (w/w) and mixing at 75° C., followed by recovering oil from said water by centrifugation.

31. The method of claim 1 wherein said stabilizing of said *Punica granatum* seed oil comprises bleaching.

32. The method of claim 1 wherein said stabilizing of said *Punica granatum* seed oil comprises bleaching by using bleaching clay.

33. The method of claim 1 wherein said stabilizing of said *Punica granatum* seed oil comprises bleaching by applying heat, adding citric acid and mixing.

34. The method of claim 1, further comprising pre-heating said *Punica granatum* seed oil to 65° C. before said stabilizing.

35. The method of claim 1 wherein said stabilizing of said *Punica granatum* seed oil comprises bleaching by adding 0.2% citric acid and mixing for 15 minutes.

36. The method of claim 1 wherein said stabilizing of said *Punica granatum* seed oil comprises bleaching by using a filter aid, adding clay or activated carbon and mixing for 15 minutes.

37. The method of claim 36 wherein said filter aid comprises cellulose acetate.

38. The method of claim 36 wherein said filter aid comprises a synthetic amorphous micronized silica hydrogel.

39. The method of claim 1 wherein said stabilizing of said *Punica granatum* seed oil comprises performing bleaching by adding clay or activated carbon to said *Punica granatum* seed oil at 0.5% to 5% w/w at 75 to 115° C. and mixing for 10 to 60 minutes in a reactor under full vacuum.

40. The method of claim 1 wherein said stabilizing of said *Punica granatum* seed oil comprises bleaching by cooling oil to 65° C. and filtering through filter elements.

* * * * *